(12) United States Patent
Malek Tabrizi et al.

(10) Patent No.: US 12,310,895 B2
(45) Date of Patent: May 27, 2025

(54) LASIK FLAP CUTTING PATTERNS INCLUDING BUBBLE BARRIER LAYER IN SIDE CUT FOR BUBBLE MANAGEMENT

(71) Applicant: AMO Development, LLC, Irvine, CA (US)

(72) Inventors: Alireza Malek Tabrizi, Fremont, CA (US); James Hill, Santa Ana, CA (US); Nima Khatibzadeh, San Jose, CA (US); Pavel Vodkin, San Jose, CA (US); Harvey Liu, Fremont, CA (US); Hong Fu, Pleasanton, CA (US); Griffith Altmann, Ladera Ranch, CA (US)

(73) Assignee: AMO Development, LLC, Irvine, CA (US)

( * ) Notice: Subject to any disclaimer, the term of this patent is extended or adjusted under 35 U.S.C. 154(b) by 444 days.

(21) Appl. No.: 17/664,034

(22) Filed: May 18, 2022

(65) Prior Publication Data

US 2022/0378615 A1     Dec. 1, 2022

Related U.S. Application Data

(60) Provisional application No. 63/192,555, filed on May 24, 2021.

(51) Int. Cl.
    *A61F 9/008*      (2006.01)

(52) U.S. Cl.
CPC ..... *A61F 9/00836* (2013.01); *A61F 2009/00851* (2013.01); *A61F 2009/00872* (2013.01); *A61F 2009/00897* (2013.01)

(58) Field of Classification Search
CPC ........ A61F 9/00836; A61F 2009/00851; A61F 2009/00872; A61F 2009/00897
See application file for complete search history.

(56) References Cited

U.S. PATENT DOCUMENTS 9,789,003 B2   10/2017   Martin
9,943,442 B2   4/2018   Krause et al.
(Continued)

FOREIGN PATENT DOCUMENTS

EP     2675408 B1   5/2017
EP     2879632 B1   10/2020
(Continued)

*Primary Examiner* — Lynsey C Eiseman
*Assistant Examiner* — Christopher J Mutchler

(57) ABSTRACT

A method implemented in an ophthalmic surgical laser system for forming a corneal flap in a patient's eye with improved bubble management. The flap includes a horizontal bed and a vertical or near vertical side cut around the periphery of the bed except for an uncut hinge area. The side cut has a bubble barrier layer that can prevent bubbles formed by the laser-tissue interaction from escaping into an interface between the corneal and the patient interface lens. In some embodiments, the bubble barrier layer is a thin uncut layer, located in the epithelium of the cornea, that separates the side cut into two portions. In other embodiments, the side cut does not reach the anterior corneal surface, leaving an uncut bubble barrier layer located with the epithelium. In other embodiments, an additional side cut portion is formed through the uncut bubble barrier layer as the last step.

18 Claims, 8 Drawing Sheets

(56) References Cited

U.S. PATENT DOCUMENTS

| | | |
|---|---|---|
| 9,962,292 B2 | 5/2018 | Bergt et al. |
| 10,369,052 B2 | 8/2019 | Fu |
| 10,492,953 B2 | 12/2019 | Bartels |
| 10,779,988 B2 | 9/2020 | Fu et al. |
| 10,792,188 B2 | 10/2020 | Malek et al. |
| 2003/0212387 A1* | 11/2003 | Kurtz ............... A61F 9/008 606/4 |
| 2016/0008173 A1* | 1/2016 | Krause ............... A61F 9/00836 606/5 |
| 2016/0067095 A1 | 3/2016 | Fu et al. |
| 2019/0175281 A1 | 6/2019 | Dishler et al. |
| 2020/0064622 A1 | 2/2020 | Rahaman et al. |

FOREIGN PATENT DOCUMENTS

| | | |
|---|---|---|
| EP | 2675392 B1 | 12/2020 |
| WO | 2012110049 A1 | 8/2012 |

* cited by examiner

LASIK FLAP CUTTING PATTERNS INCLUDING BUBBLE BARRIER LAYER IN SIDE CUT FOR BUBBLE MANAGEMENT

CROSS REFERENCE TO RELATED PATENT APPLICATIONS

This application claims the benefit under 35 U.S.C. § 119(e) of U.S. Provisional Patent Application No. 63/192,555, filed May 24, 2021, which is incorporated herein by reference in its entirety.

BACKGROUND OF THE INVENTION

Field of the Invention

This invention relates to ophthalmic laser surgeries, and in particular, it relates to flap cutting in LASIK (laser-assisted in situ keratomileusis) surgeries using a femtosecond laser.

Description of Related Art

Femtosecond lasers are used to cut flaps in the corneal stroma as the first step of LASIK (laser-assisted in situ keratomileusis) surgeries. A flap is typically formed by a horizontal bed cut which is parallel to the anterior corneal surface and a vertical or near vertical side cut around the periphery of the bed cut expect for an uncut hinge region.

When using femtosecond lasers to cut flaps in the corneal stroma as a part of a LASIK procedure, the interaction of the laser pulses with the tissue can sometimes create excessive gas bubbles which can interfere with the continued cutting of the tissue, creating tissue bridges and rough bed cut surfaces. To obtain the best tissue cutting quality, it is critical to manage gas bubbles generated during laser tissue interactions, so that the gas bubbles will not cause uncut tissue islands in the flap bed and uncut tags in the flap side cut.

SUMMARY

The present invention is directed to a method and related apparatus for incising a corneal flap in a LASIK surgery that substantially obviates one or more of the problems due to limitations and disadvantages of the related art.

Embodiments of this invention provide flap cutting patterns where the side cut has an uncut bubble barrier layer or other features to prevent or reduce bubbles escaping into the interface between the cornea and the patient interface device of the laser system.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides a method implemented in an ophthalmic surgical laser system for incising a cornea of a patient's eye to form a corneal flap, the patient's eye being coupled to a patient interface device of the ophthalmic surgical laser system, the method including: controlling a laser delivery system of the ophthalmic surgical laser system to deliver a pulsed laser beam to the cornea; controlling the laser delivery system to scan the pulsed laser beam to form a bed of the flap in the cornea at a predefined bed depth; and controlling the laser delivery system to scan the pulsed laser beam to form a side cut, wherein the side cut extends in lateral directions along a periphery of the bed except for a hinge portion, and extends in a depth direction from the bed depth to an anterior corneal surface, wherein the side cut defines a lower portion and an upper portion separated by an uncut bubble barrier layer, wherein the bubble barrier layer is located within an epithelium of the cornea, and wherein the upper portion of the side cut intersects the anterior corneal surface.

The bubble barrier layer preferably has a thickness of between 5 and 20 microns. The bubble barrier layer may be implemented using laser blanking when forming the side cut.

In another aspect, the present invention provides a method implemented in an ophthalmic surgical laser system for incising a cornea of a patient's eye to form a corneal flap, the patient's eye being coupled to a patient interface device of the ophthalmic surgical laser system, the method including: controlling a laser delivery system of the ophthalmic surgical laser system to deliver a pulsed laser beam to the cornea; controlling the laser delivery system to scan the pulsed laser beam to form a bed of the flap in the cornea at a predefined bed depth; and controlling the laser delivery system to scan the pulsed laser beam to form a side cut, wherein the side cut extends in lateral directions along a periphery of the bed except for a hinge portion, and extends in a depth direction from the bed depth to a predefined depth below an anterior corneal surface without intersecting the anterior corneal surface, wherein the predefined depth is between 5 and 20 microns.

In another aspect, the present invention provides a method implemented in an ophthalmic surgical laser system for incising a cornea of a patient's eye to form a corneal flap, the patient's eye being coupled to a patient interface device of the ophthalmic surgical laser system, the method including: controlling a laser delivery system of the ophthalmic surgical laser system to deliver a pulsed laser beam to the cornea; controlling the laser delivery system to scan the pulsed laser beam to form a bed of the flap in the cornea at a predefined bed depth; controlling the laser delivery system to scan the pulsed laser beam to form a first side cut portion, wherein the first side cut portion extends in lateral directions along a periphery of the bed except for a hinge portion, and extends in a depth direction from the bed depth to a second predefined depth below an anterior corneal surface without intersecting the anterior corneal surface, the second predefined depth being within an epithelium of the cornea; and after forming the bed and the first side cut portion, controlling the laser delivery system to scan the pulsed laser beam to form a second side cut portion, wherein the second side cut portion extends in lateral directions along a periphery of the bed except for a hinge portion, and extends in a depth direction to connect the first side cut portion to the anterior corneal surface. The second side cut portion may be aligned with and extends in the same direction as the first side cut portion, or extends at a different angle from the first side cut portion and intersects the first side cut portion along the periphery of the flap.

In other aspects, the present invention provides an ophthalmic surgical laser system which includes a laser source configured to generate a laser beam, a laser delivery system configured to deliver the laser beam to a cornea of a patient's eye, and a controller configured to control the laser source and the laser delivery system to perform one or more of the above described methods.

It is to be understood that both the foregoing general description and the following detailed description are exemplary and explanatory and are intended to provide further explanation of the invention as claimed.

DETAILED DESCRIPTION OF PREFERRED EMBODIMENTS

Figure 1:
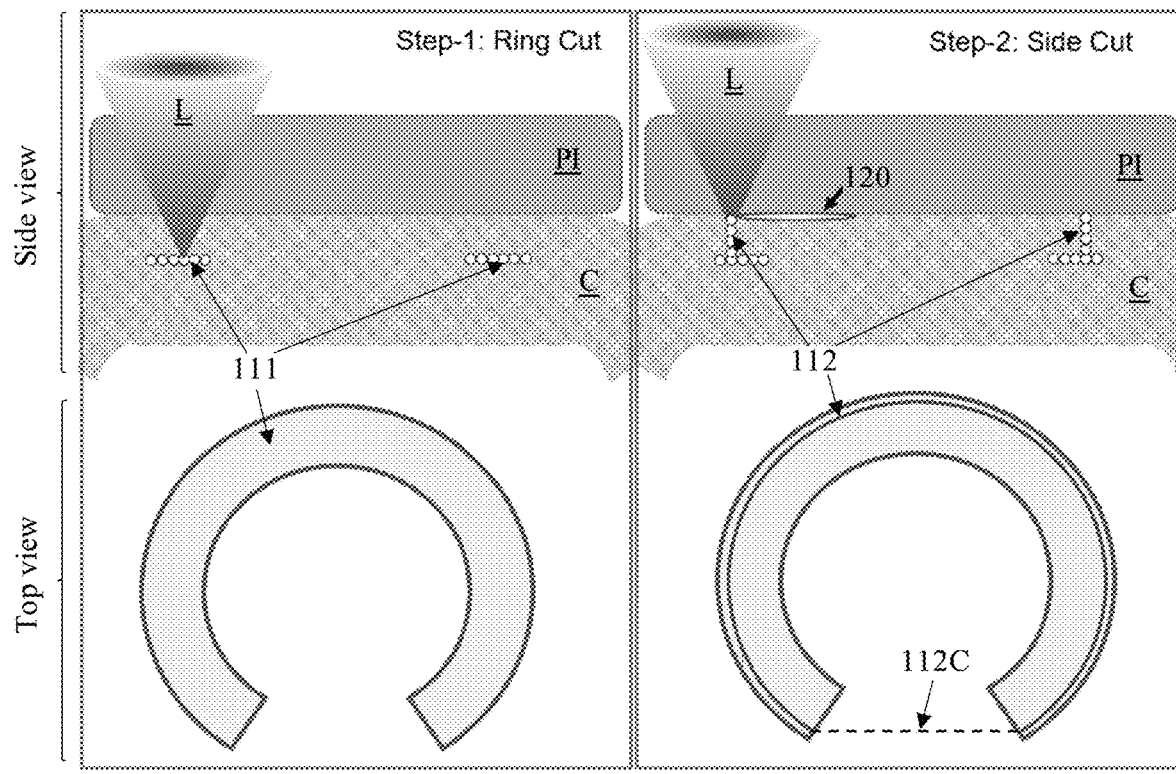
FIG. 1 schematically illustrates a process for forming a flap in a patient's cornea using an ophthalmic laser system.
Figure 1:
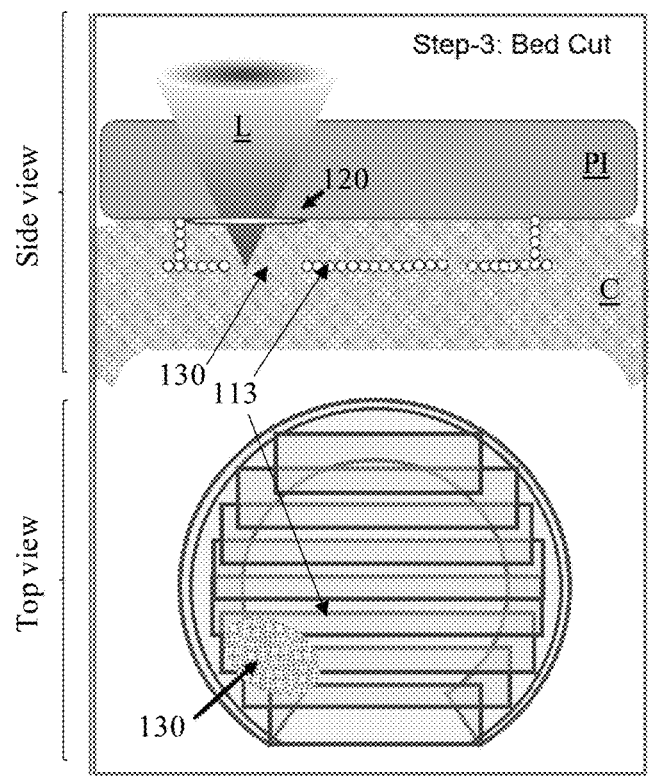

A corneal flap in a LASIK surgery is typically formed by a horizontal bed cut which is parallel to the anterior corneal surface and a vertical or near vertical side cut along the periphery of the bed cut expect for an uncut hinge region. FIG. 1 illustrates an exemplary cutting order for forming a flap in a patient's cornea C, where a horizontal ring cut 111 is formed first (Step-1: Ring Cut) at the bed level to define a periphery of the bed, followed by a side cut 112 extending vertically or near vertically from the bed level to the anterior corneal surface (Step-2: Side Cut), then followed by a bed cut 113 that forms the central portion of the bed surrounded by the ring cut (Step-3: Bed Cut). The ring cut 111 and bed cut 113 together form the bed of the flap. The side cut 112 extends along the periphery of the bed (slightly smaller than the outer edge of the bed in this example) except for an uncut portion in a defined angular range, indicated by the dashed line 112C in Step-2, which forms a hinge that keeps the flap connected to the remaining portion of the cornea. The ring cut 111 has a corresponding uncut gap in the hinge area. FIG. 1 also shows a patient interface lens PI which is used to couple the patient's eye to the laser beam delivery optical system during the laser surgery. As seen in FIG. 1, the patient interface lens PI contacts and flattens the cornea C.

In FIG. 1, the side views are cross-sectional views in a plane that passes through the optical axis, and the top views are cross-sectional views in a lateral (horizontal) plane perpendicular to the optical axis.

Under certain circumstances, such as high pulse energy and when the side cut angle is 90° or greater (i.e., vertical or inclined in the side view), bubbles generated during the side cut and/or ring cut may be released to the interface between patient interface lens PI and the cornea C, which may block or scatter the laser beam L and cause uncut tissue island in the subsequently formed bed cut or parts of the side cut. In the example shown in FIG. 1, a bubble 120 is released through the side cut and is present at the PI-cornea interface, and interferes with the laser beam L during the bed cut step (Step-3), resulting in an uncut tissue island 130 in the bed cut. Even if a different cutting order is used, where the side cut 112 is formed after the bed cut 113, bubbles generated when forming some portions of the side cut can be released to the PI-cornea interface and interfere with the cutting of other segments of the side cut. Such uncut islands in the bed cut or side cut degrade the quality of the flap formation, causing difficult or incomplete separation of the flap from the cornea.

To solve these problems, some embodiments of the present invention introduce a bubble barrier layer in the side cut, which is a thin uncut band, to prevent bubbles generated during the ring cut, and/or the bed cut, and/or most parts of the side cut from escaping to the PI-cornea interface and blocking the laser beam during the flap cutting process. The bubble barrier layer is manually broken with a flap lifting tool when the surgeon lifts the flap from the cornea.

Figure 2A:
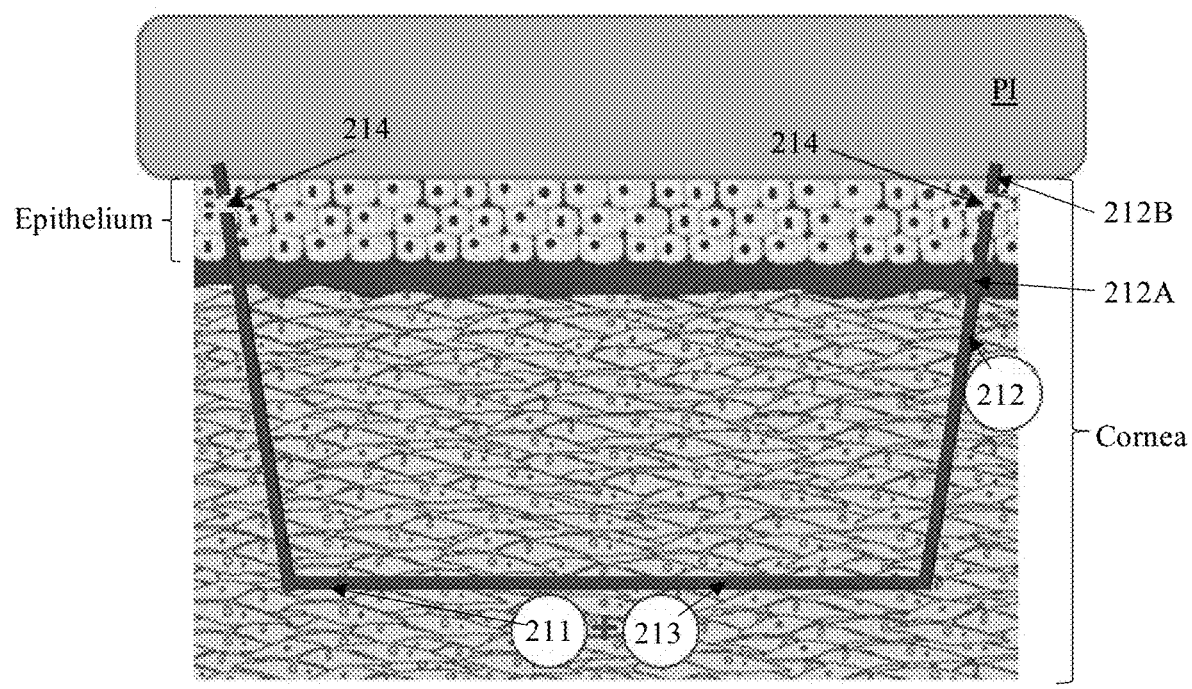
FIGS. 2a and 2b schematically illustrate a method for forming a corneal flap that includes a bubble barrier layer in the side cut according to a first embodiment of the present invention.
Figure 2B:
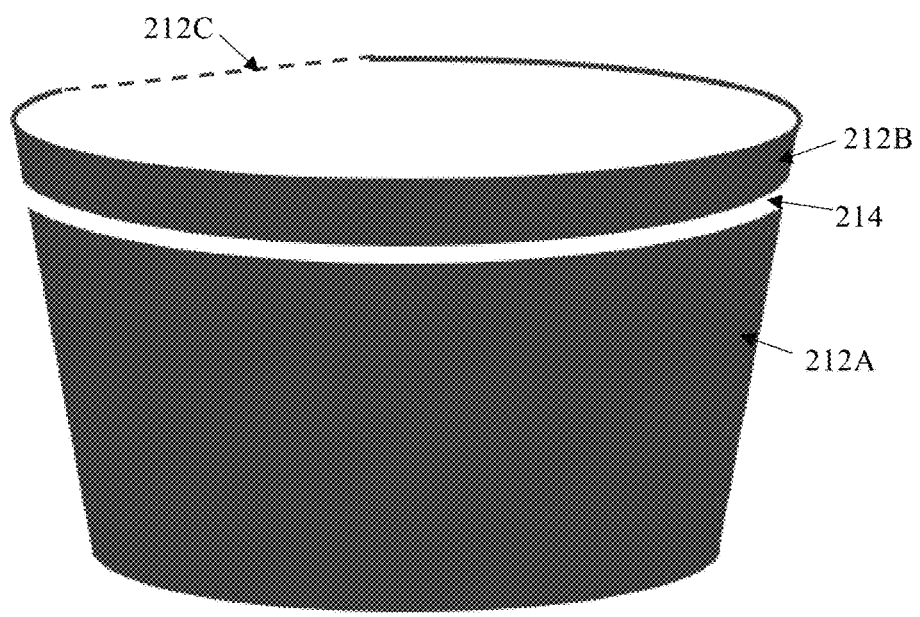

FIG. 2a (side cross-sectional view) and FIG. 2b (schematic 3D view) illustrate a method that implements a bubble barrier layer in the side cut for a corneal flap according to a first embodiment of the present invention. The flap incisions include a horizontal ring cut 211 formed at the bed level to define a periphery of the bed, a side cut 212 extending in the depth direction vertically or near vertically from the bed level to the anterior corneal surface, and a bed cut 213 that forms the central portion of the bed surrounded by the ring cut. The side cut 212 extends along the periphery of the flap except for an uncut portion in a defined angular range, indicated by the dashed line 212C, which forms the hinge of the flap. FIG. 2a also shows a patient interface lens PI of the laser beam delivery optical system that contacts the cornea C.

The bubble barrier layer 214 is an uncut gap in the side cut 212, extending along the entire lateral extent of the side cut, separating the side cut into a lower portion 212A and an upper portion 212B. As a result, the lower portion 212A of the side cut below the bubble barrier layer 214 is separated from the anterior corneal surface by the bubble barrier layer, so that bubbles generated within the lower portion 212A as well as the ring cut 211 and bed cut 213 do not escape to the PI-cornea interface. The upper portion 212B of the side cut above the bubble barrier layer intersects the anterior corneal surface.

In this example, the bubble barrier layer 214 is located at a uniform distance from the anterior corneal surface along the entire lateral extent of the side cut. Preferably, the bubble barrier layer 214 is located near the anterior corneal surface, for example, within the epithelium layer of the cornea (which is typically 50 to 52 microns thick). Preferably, the top of the bubble barrier layer 214 is between 2 and 10 microns from the anterior corneal surface. The thickness of the bubble barrier layer (i.e. the width of the gap) is preferably a few microns, for example, 10 microns, or more generally, 5 to 20 microns. The bubble barrier layer should be thick enough to prevent the bubbles from coming out of the cornea, yet thin enough to not cause significant side cut separation problem when the surgeon manually lifts the flap.

One advantage of forming the bubble barrier layer entirely within the epithelium layer is that the epithelium is relatively easy to break when the surgeon manually lift the flap. In most situations, the side cut, with the accumulated bubbles, will be readily visible from the surface even with the bubble barrier layer present, and the surgeon will often not even notice the thin bubble barrier layer when separating the flap.

The ring cut 211 and bed cut 213 may be similar to the ring cut 111 and bed but 113 in FIG. 1, respectively, and collectively form the bed of the flap. The cutting sequence of the ring cut 211, side cut 212 and bed cut 213 is not limited to any particular sequence. For example, the side cut 212 may be formed either after or before the bed cut 213 or the ring cut 211. Note that if no bubble barrier layer is present, and when the side cut 212 is formed last, the bubbles present at the PI-cornea interface will not interfere with the bed cut or ring cut, but can still interfere with forming the side cut itself because cutting of the side cut proceeds in a circumferential direction, as will be described in more detail later (see FIG. 3), so bubbles formed when cutting one angular portion of the side cut may escape and interfere with the laser beam when cutting another angular portion of the side cut.

In a preferred embodiment, the bubble barrier layer 214 is formed by applying laser blanking (i.e., laser blocking) in predefined depth ranges when scanning the laser beam or a short laser scan line in the vertical direction along the side cut.

Figure 3:
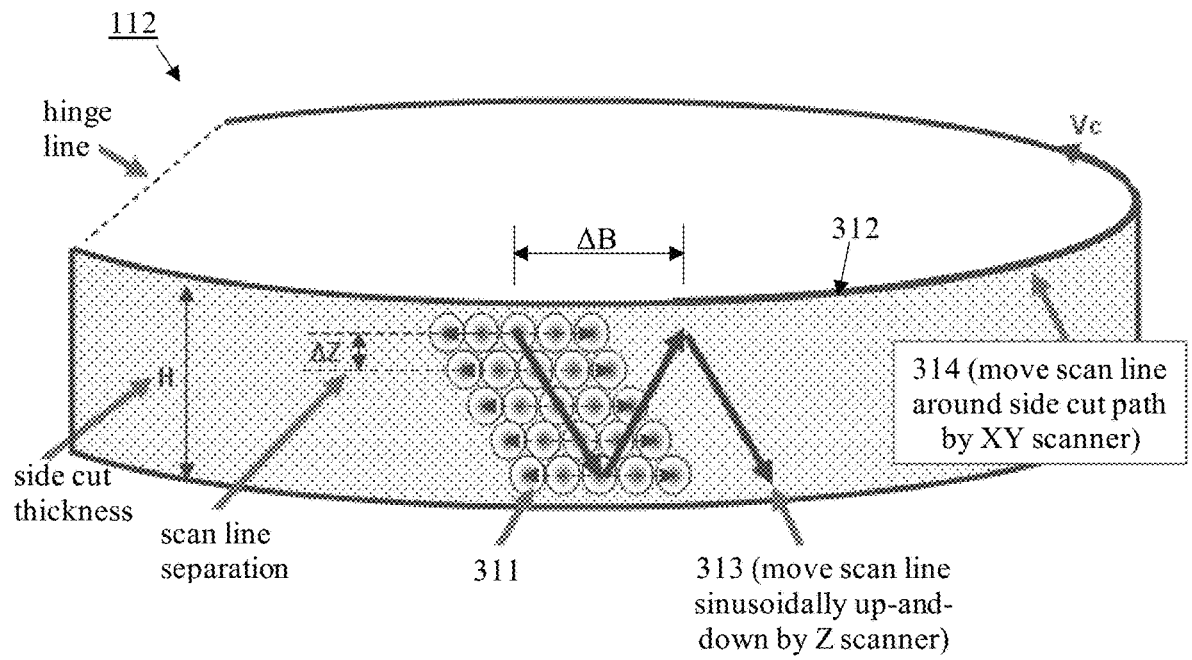
FIG. 3 schematically illustrates a method of forming a side cut using a fast-scan-slow-sweep technique, by sweeping a laser scan line generated by a resonant scanning femtosecond laser.

As described in more detail later, in preferred embodiments, the laser pulse pattern generated by the ophthalmic laser system is in the form of a short laser scan line, which is a line of focused laser pulses formed by a resonant scanner. The direction of the scan line is in the lateral plane (i.e. XY plane, perpendicular to the optical axis) and can be rotated by a scan line rotator, and the center position of the scan line is moved by an XY scanner in the two lateral directions and also by a Z scanner in the depth direction. Thus, the scan line can be rotated and swept in three dimensions to form various cuts in the cornea. This is referred to as the fast-scan-slow-sweep scanning scheme. To form the side cut 112 or 212, as shown in FIG. 3, the laser scan line 311 is placed tangent to the side-cut path (which is along the circumference of the flap) 312, and is moved sinusoidally in the Z direction 313, simultaneously moved around the side-cut path in the circumferential XY direction 314, and simultaneously rotated to keep it tangent to the side-cut path 312. The depth Z of the scan line as a function of time (measured from the center depth of the side cut in this example) is given by:

$$Z(t) = \frac{H}{2}\sin(2\pi \cdot f_z \cdot t), f_z = \frac{\Delta_z}{H}f_s, V_c = \Delta B \cdot f_z$$

where H is the side cut thickness, $f_z$ is the Z scan frequency, $f_s$ is the resonant scan frequency that produces the scan line, $\Delta_z$ is a scan line-to-line separation parameter, $V_c$ is the speed of the XY scan in the circumferential direction, and $\Delta B$ is a band-to-band separation of the band in the circumferential direction in one period of the Z scan. Preferably, during the anterior to posterior (or the posterior to anterior) half of each sinusoidal period, the laser beam is fast blanked, e.g. blocked by using an acousto-optic modulator of the laser system.

To form a side cut with a non-vertical angle, the scan line center position is oscillated simultaneously and synchronously in both the radial direction in the XY plane and in the Z direction, such that the radial position is at a minimum (or maximum) value when the Z position is at the bottom of the side cut, and at a maximum (or minimum) value when the Z position is at the top of the side cut. Further details of methods of forming a side cut having non-vertical sides are described in U.S. Pat. Appl. Pub. No. 2016/0067095, entitled Systems and Methods for Synchronized Three-Dimensional Laser Incisions.

Note that FIG. 3 does not show the bubble barrier layer; it only illustrates a general method of forming a side cut or a portion of the side cut. This scanning method may be used to form a conventional side cut without a bubble barrier layer, or used in conjunction with laser blanking to form a side cut with a bubble barrier layer according to embodiments of the present invention.

Figure 4:
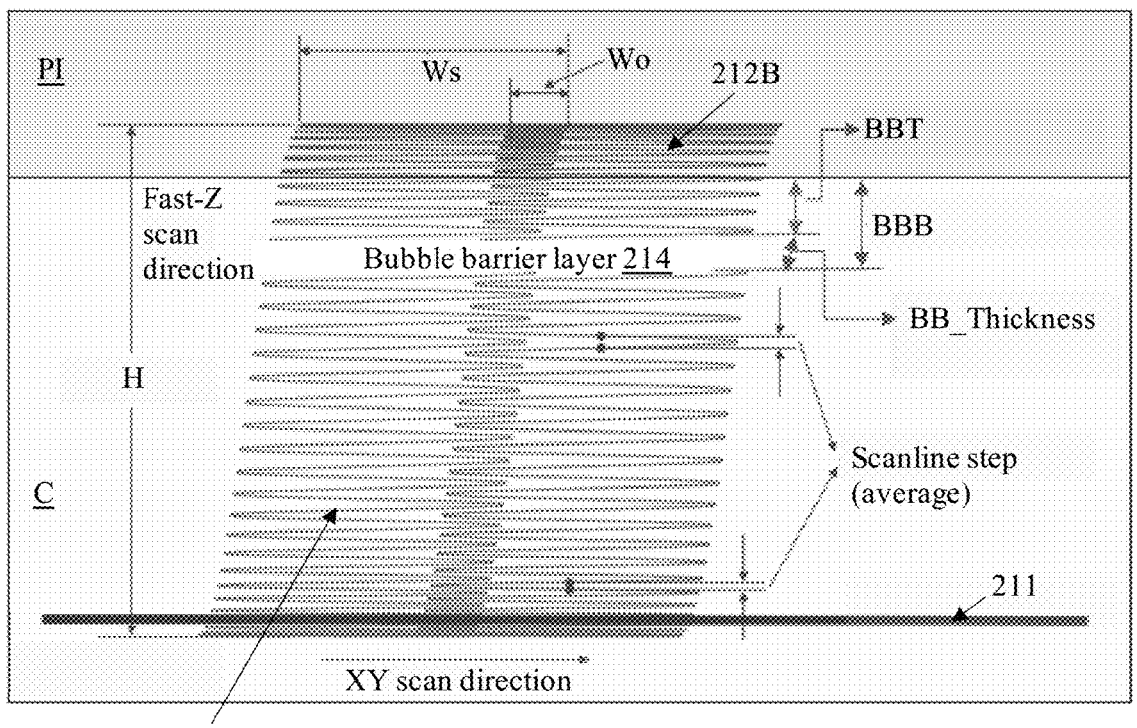
FIG. 4 schematically illustrates a method using fast-scan-slow-sweep scanning with laser blanking to form the side cut with bubble barrier layer in the first embodiment.

FIG. 4 schematically illustrates the fast-scan-slow-sweep scanning scheme used to form the side cut with a bubble barrier layer in the embodiment of FIGS. 2a and 2b, showing two sweeps of the scan line with laser blanking to implement the bubble barrier layer 214. Note that in this example, the side cut pattern 212 extends slightly below the depth of the ring cut 211, and also extends slightly above the anterior corneal surface into the PI lens. Such overcut (optional) ensures complete tissue separation at the intersection of the side cut and ring cut and at the intersection of the side cut and the anterior corneal surface. FIG. 4 also shows that the adjacent sweeps, each having a scan line width Ws, overlap each other by an amount Wo. It can also be seen that due to the sinusoidal function of the Z scan Z(t), the scan line step, i.e., distance between adjacent scan lines in the sweep, is not uniform in the depth direction.

Figure 5:
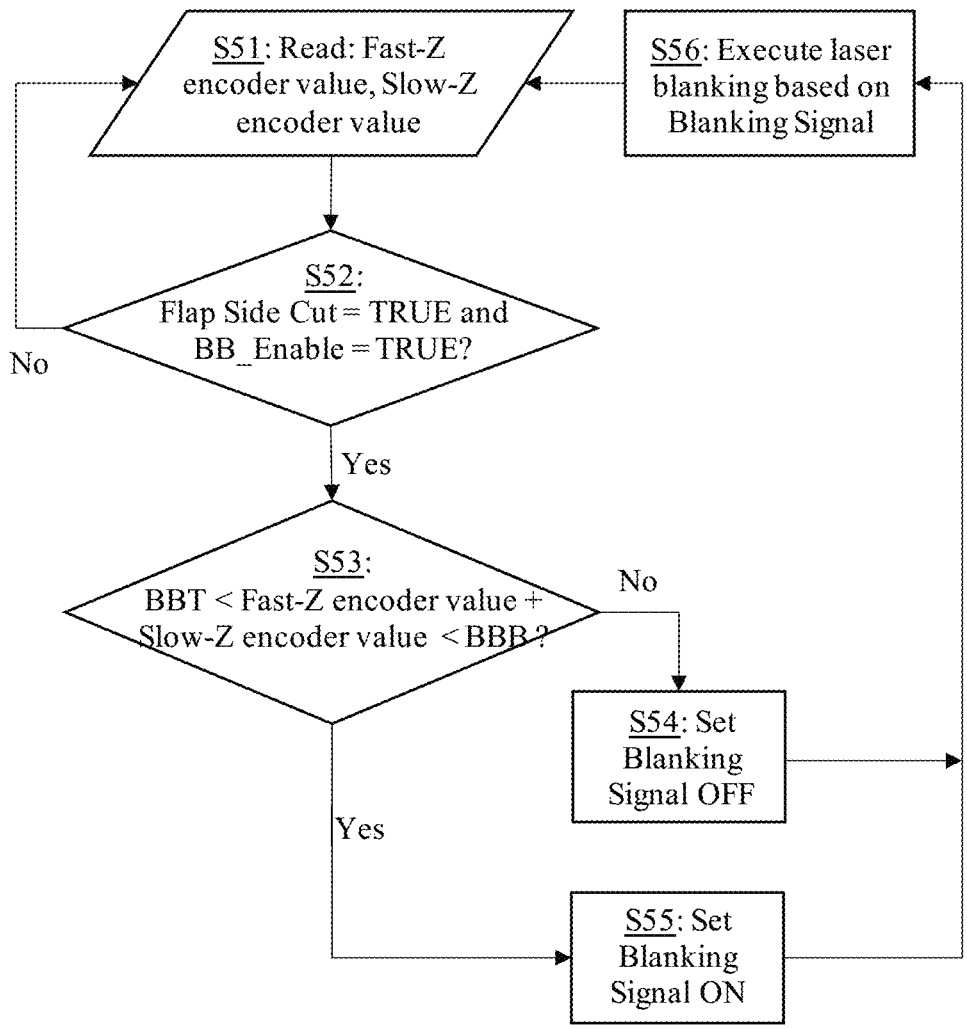
FIG. 5 is a flow chart showing a control logic for performing laser blanking to form the side cut with bubble barrier layer in the first embodiment.

FIG. 5 is a flow chart illustrating a control method implemented in a controller of the ophthalmic laser system for performing laser blanking to form a side cut with a bubble barrier layer such as that shown in FIG. 4. The laser blanking control is performed while the laser system is executing a laser incision pattern. As shown in FIG. 5, the laser blanking control process reads the Z encoder value, which is the depth (Z) position of the laser scan line (step S51). As will be described in more detail later, the ophthalmic laser system may include two Z scanners, namely a fast-Z scanner and a slow-Z scanner, and the Z position of the scan line may be the combination of the two Z encoder values. The process then determines whether a "Flap Side Cut" flag is true, i.e., whether the system is currently executing a flap side cut (as opposed to, for example, a bed cut), and whether a "BB Enable" flag is true, i.e., whether the cutting pattern is set to implement a bubble barrier layer (step S52). If either condition is not true, no laser blanking will be executed and the process returns to step S51. If both conditions are true, the process determines whether the Z encoder value (in this example, the sum of the fast-Z encoder value and the slow-Z encoder value) falls between a bubble barrier top Z position (BBT) and a bubble barrier bottom Z position (BBB) (step S53). Depending on whether or not the Z encoder value falls between BBT and BBB, a blanking signal is set to ON (step S55) or OFF (step S54). The controller controls the laser system hardware to execute laser blanking based on the blanking signal being ON or OFF (step S56). The blanking of the laser results in uncut regions which constitute the bubble barrier layer 214.

BBB and BBT are process parameters that may be based on user input. In some implementations, the user input includes BBB and a bubble barrier layer thickness (BB_Thickness), and BBT is calculated using BBB=BBT+ BB_Thickness. Alternatively, BBT may be calculated from user inputted BBB and BB_Thickness. In this example, BBB and BBT are defined as distances from the anterior corneal surface, as shown in FIG. 4.

Figure 6:
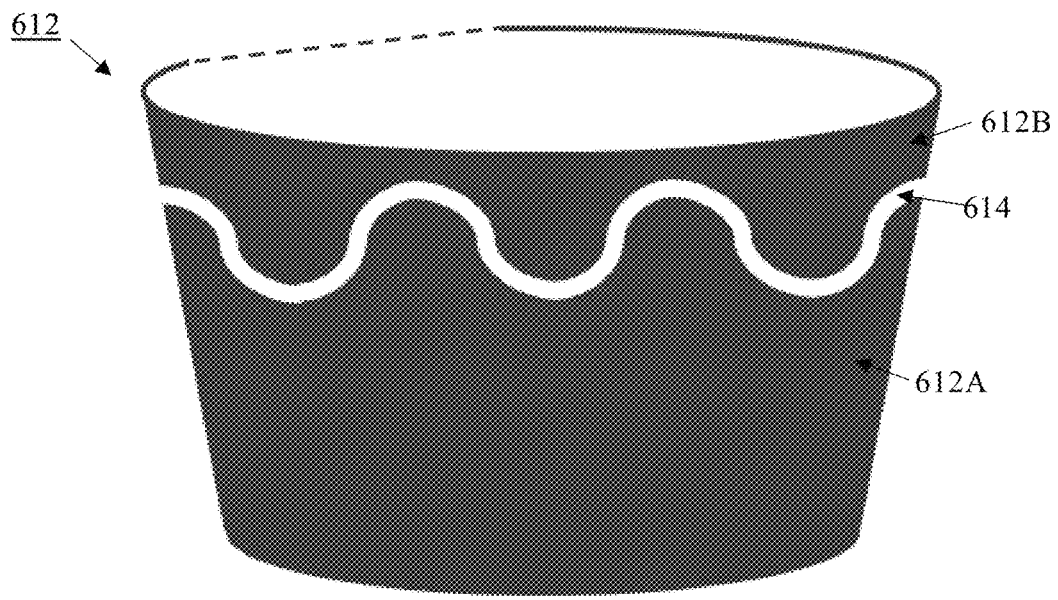
FIG. 6 schematically illustrate a side cut for a corneal flap that implements a bubble barrier layer according to a second embodiment of the present invention.

FIG. 6 (schematic 3D view) illustrates a side cut 612 for a corneal flap that implements a bubble barrier layer 614 according to a second embodiment of the present invention. The various flap incisions in the second embodiment are similar to the corresponding ones of the first embodiment, except that in the second embodiment, the bubble barrier layer 614 is placed at variable depths from the anterior corneal surface. In the illustrated example, the variable depth is a wave pattern extending in the angular direction. Preferably, the bubble barrier layer 614 is located entirely within the epithelium. Similar to the embodiment of FIGS. 2a and 2b, the lower portion 612A of the side cut is separated from the anterior corneal surface by the bubble barrier layer 614, and the upper portion 612B of the side cut intersects the anterior corneal surface. An advantage of this bubble barrier layer shape is that it distributes the tissue tear associated with the manual breaking of the bubble barrier layer into different depths. It may also facilitate the manual separation of the flap along the side cut because the tip of the surgeon's flap lifting tool can break the bubble barrier layer by moving either vertically or horizontally.

To implement the second embodiment, a laser blanking control process similar to that shown in FIG. 5 may be used, with the following modifications. In step S51, the process additionally reads the X and Y positions, or alternatively an angular position, of the center of the laser scan line. In step S53, the BBT and BBB values used in the evaluation are functions of the X and Y positions or angular position of the laser scan line.

In the embodiments shown FIGS. 2a, 2b and 6, the bubble barrier layer 214 and 614 have a uniform thickness. In alternative embodiments (not shown in the drawings), the bubble barrier layer may have non-uniform thicknesses along the angular direction.

Figure 7:
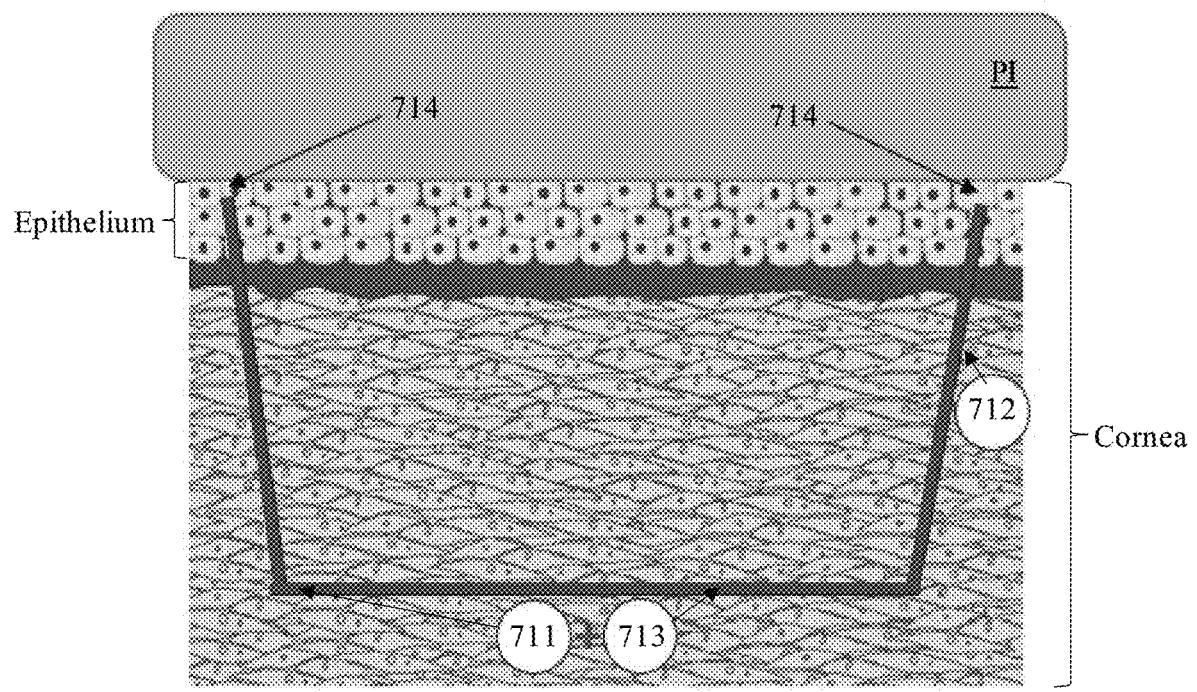
FIG. 7 schematically illustrates a corneal flap with a side cut that implements a bubble barrier layer according to a third embodiment of the present invention.

FIG. 7 (side cross-sectional view) illustrates a corneal flap with a side cut 712 that implements a bubble barrier layer 714 according to a third embodiment of the present invention. The ring cut 711, bed cut 713 and side cut 712 are similar to the corresponding cuts in the first embodiment, except that in this embodiment, the bubble barrier layer 714 is an uncut layer of the side cut located at the top surface of the epithelium. In other words, the side cut 712 does not reach the anterior corneal surface. The thickness of the uncut bubble barrier layer 714 is preferably 5 to 20 microns, for example, 10 microns. In this embodiment, even though it does not reach the anterior corneal surface, the side cut will be readily visible to the surgeon due to internal bubbles and other optical effect of tissue disruption in the side cut, so that the surgeon can still accurately use the flap lifting tool to break the bubble barrier layer and lift the flap.

To implement the third embodiment, a laser blanking control process similar to that illustrated in FIG. 5 may be used, but with the bubble barrier top position BBT set at zero or at a distance above the anterior corneal surface. Alternatively, the scan pattern for the side cut may be set so that the slow-sweeps stop at the Z position of BBB.

Figure 8:
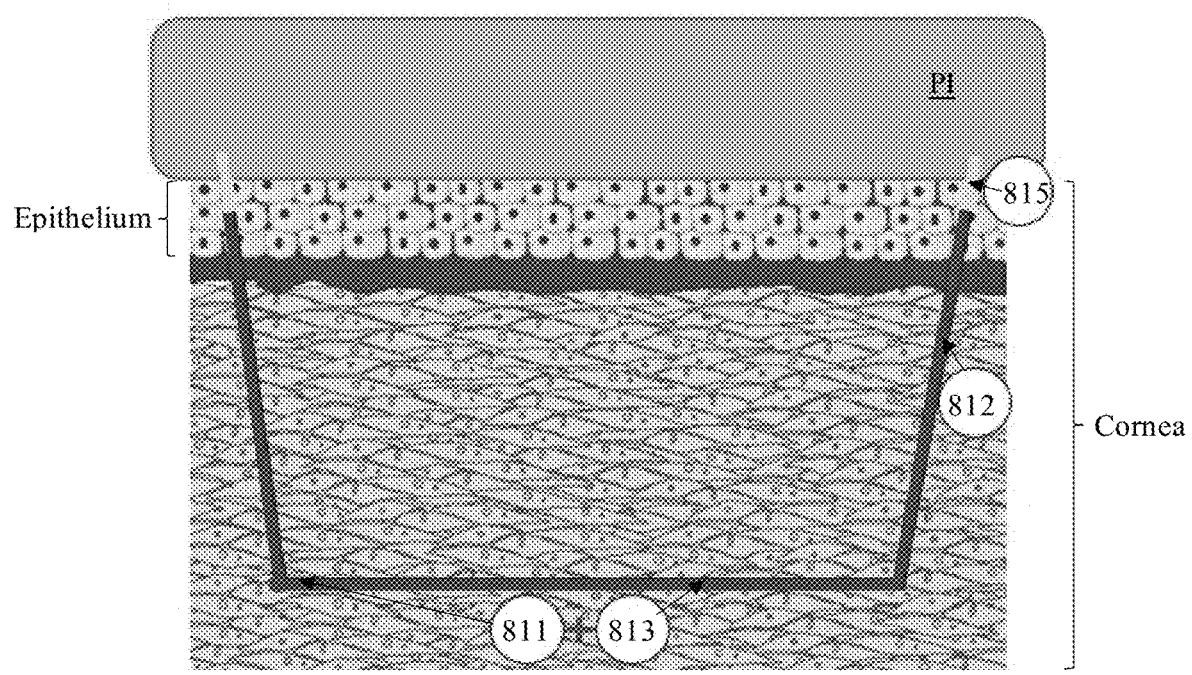
FIG. 8 schematically illustrates a method for forming a side cut for a corneal flap according to a fourth embodiment of the present invention.

FIG. 8 (side cross-sectional view) illustrates a method for forming a side cut for a corneal flap according to a fourth embodiment of the present invention. In this embodiment, the ring cut 811 and bed cut 813 are similar to the corresponding cuts in the first embodiment, but the side cut is formed in two steps. The first step forms a first side cut portion 812 similar to the side cut 712 in the third embodiment (FIG. 7), i.e., the first side cut portion 812 does not reach the anterior corneal surface. The thickness of the uncut bubble barrier layer above the first side cut portion 812 is preferably 5 to 20 microns, for example, 10 microns. After the ring cut 811, the first side cut portion 812 and the bed cut 813 are formed (in any order), an additional side cut portion 815 is formed through the bubble barrier layer to connect the first side cut portion 812 to the anterior corneal surface. The additional side cut portion 815 is aligned with and extends in the same vertical or near vertical direction as the first side cut portion 812. The first side cut portion 812 and the additional side cut portion 815 together form the side cut of the flap. Using this method, bubbles are prevented from escaping and interfering with the cutting of the ring cut 812, the first side cut portion 812 and the bed cut 813; meanwhile, the overall side cut can still reach the anterior corneal surface, so that the surgeon does not need to manually break a bubble barrier layer. A potential disadvantage of this method is that the additional side cut portion 815 may not exactly connect with the first side cut portion 812 due to registration error, resulting in tear between the two side cuts portions when the surgeon opens the side cut.

To implement the fourth embodiment, both side cut portions 812 and 815 may be formed using the method shown in FIG. 3 without laser blanking.

Figure 9:
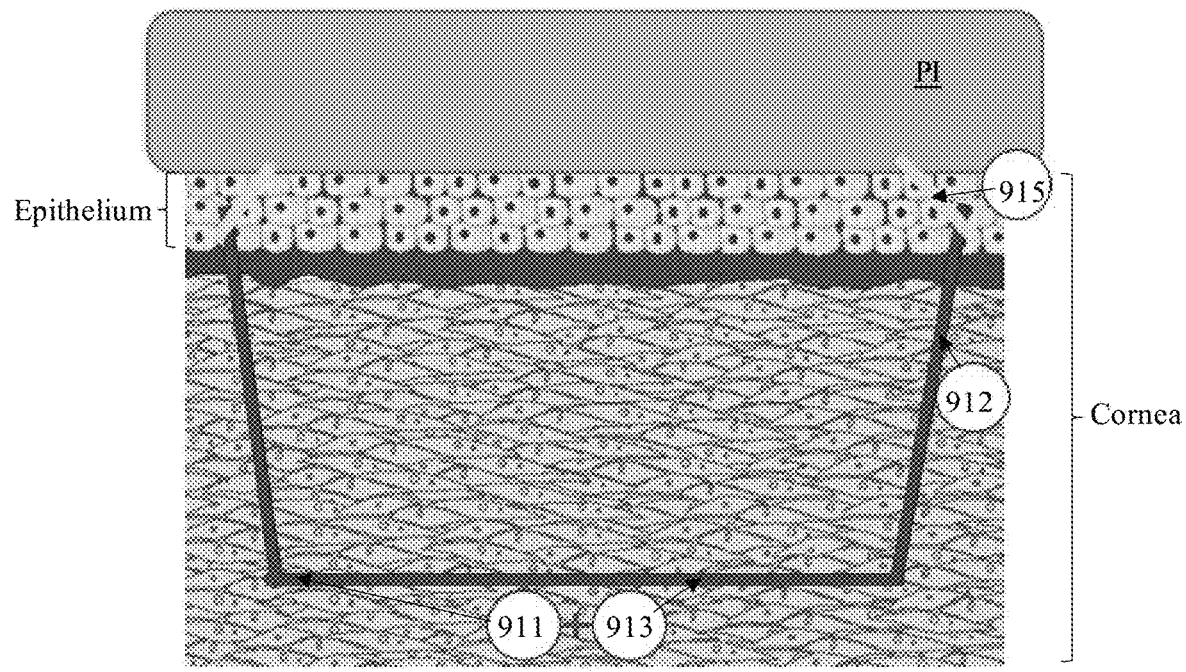
FIG. 9 schematically illustrates a method for forming a side cut for a corneal flap according to a fifth embodiment of the present invention.

FIG. 9 (side cross-sectional view) illustrates a method for forming a side cut for a corneal flap according to a fifth embodiment of the present invention. This embodiment is similar to the fourth embodiment shown in FIG. 8, except that the additional side cut portion 915 is formed at a different angle (in the side view) from the first side cut portion 912, and the two side cut portions 912 and 915 intersect each other along the periphery of the flap. In the illustrated embodiment, the first side cut portion 912 and the additional side cut portion 915 are inclined on opposite sides of the vertical direction. Preferably, the additional side cut portion 915 is located within the epithelium of the cornea. An advantage of this embodiment, as compared to the fourth embodiment shown in FIG. 8, is that it can tolerate certain amount of misalignment between the first side cut portion 912 and the additional side cut portion 915. For example, if the additional side cut portion 915 is shifted laterally slightly, it will still intersect the first side cut portion 912. The ring cut 911 and bed cut 913 are similar to the corresponding cuts in the first embodiment.

Figure 10A:
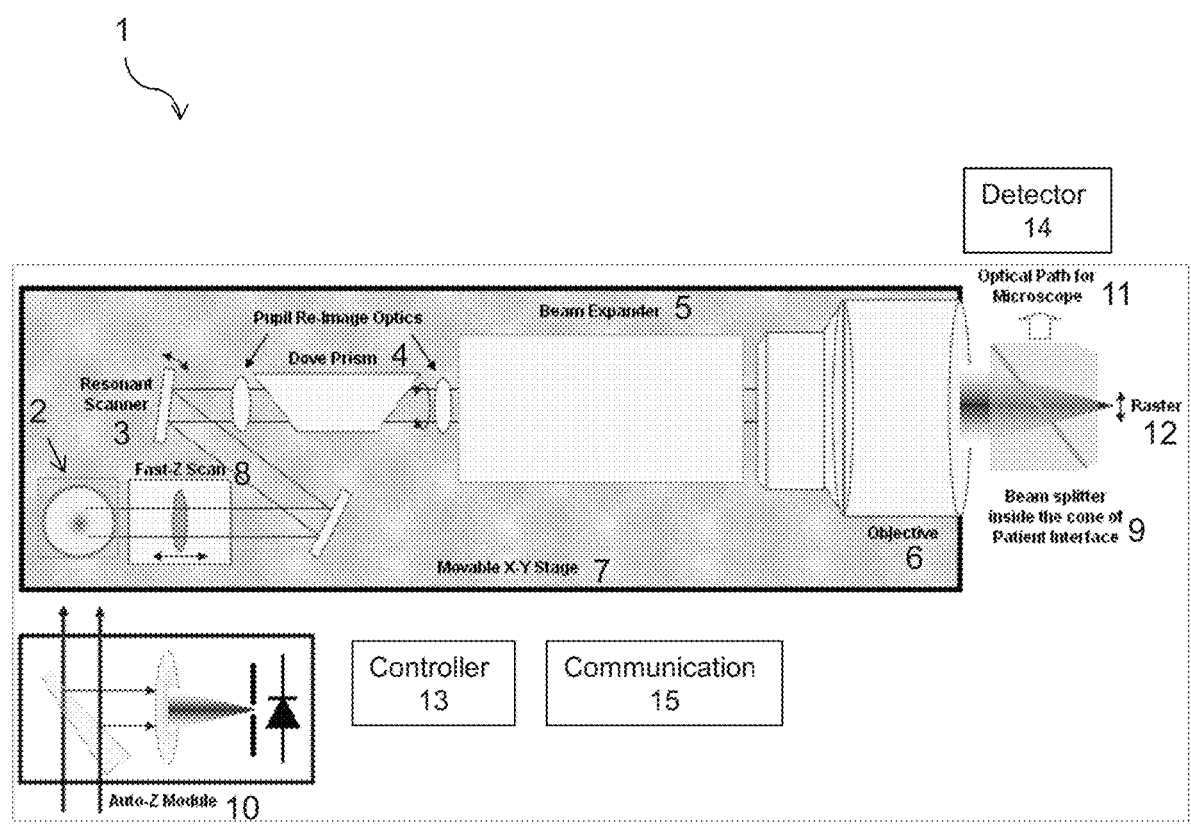
FIGS. 10A and 10B schematically illustrate two exemplary ophthalmic laser systems which may be used to implement embodiments of the present invention.
Figure 10B:
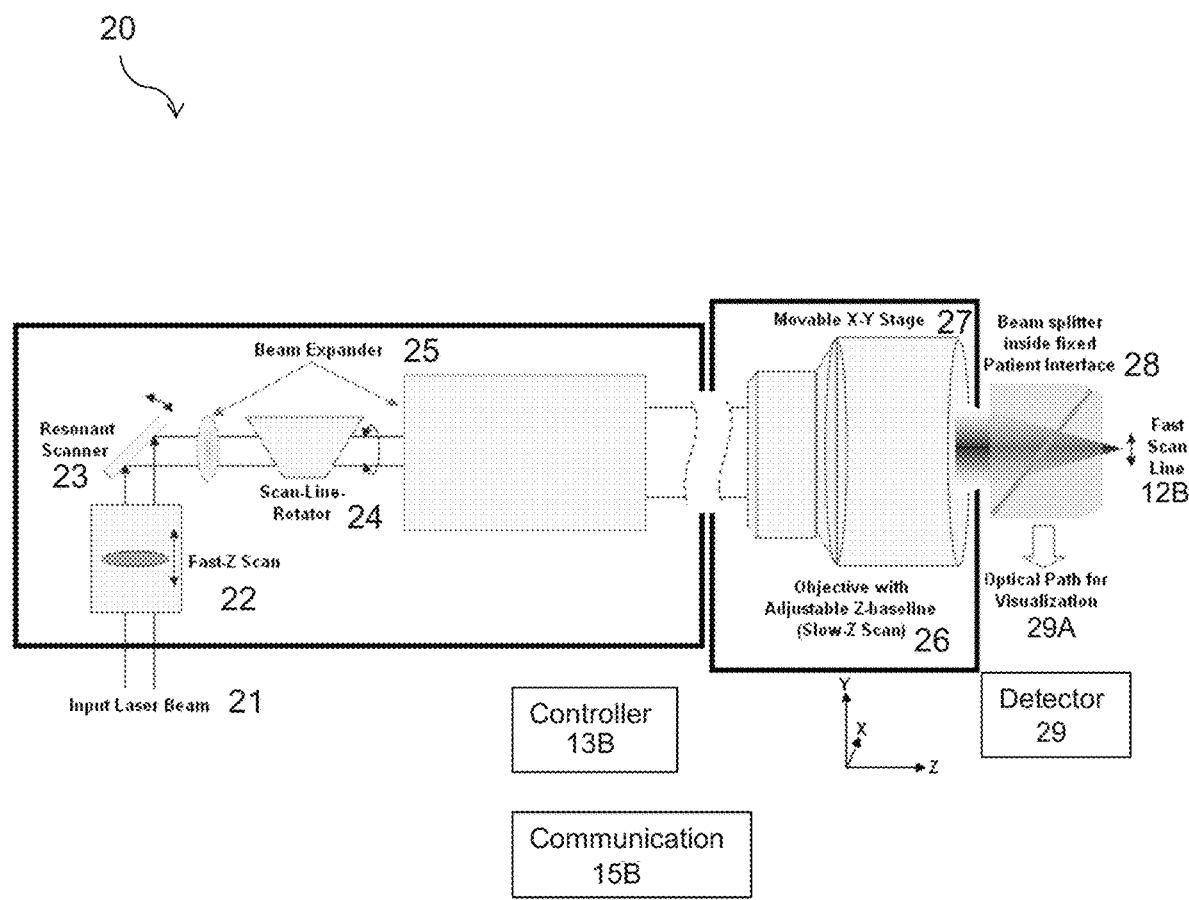

Ophthalmic laser systems that may be used to implement the above-described flap formation procedures are described in more detail now with reference to FIGS. 10A and 10B.

FIG. 10A shows an ophthalmic surgical laser system 1 suitable for making an incision in a target material such as a cornea of an eye. A laser 2, such as a femtosecond laser, provides a pulsed laser beam 2A which may be used in optical procedures to treat the eye. The system 1 further includes, but is not limited to, a high frequency scanner (such as a resonant scanner) 3 for scanning the pulsed laser beam to produce a scan line 12 of the pulsed laser beam, a scan line rotator 4 for rotating the scan line 12, a beam expander 5, an objective 6 for focusing the laser beam, an XY scan device 7 for deflecting or directing the laser beam on or within the target, a fast-Z scan device 8, a patient interface 9, an auto-Z device 10, a controller 13, and a communication module 15.

The resonant scanner 3 scans the pulsed laser beam at a high resonant frequency (e.g., thousands of Hz) to produces the scan line that extends in a lateral orientation (i.e. a direction perpendicular to the laser beam propagation direction Z) and having a desired length, for example, between 1 mm and 2 mm. The length of the scan line may be adjustable. The scan line rotator 4 may be implemented by a Dove prism, a Pechan prism, a set of mirrors, or the like, mounted on a rotating stage. By rotating the scan line rotator 4 around the Z axis, the lateral orientation of the scan line 12 is rotated, so that the scan line may be placed at any desired orientation in the XY plane (i.e., the lateral plane perpendicular to the laser beam propagation direction Z). The XY scan device 7 may be a movable XY scanning stage having the focusing objective 6 mounted thereon; the XY scan device 7 carries the objective 6 and moves it relative to the patient interface device 9, so as to move the center of the scan line 12 relative to the patient's eye in the XY directions. The fast-Z scan device 8 changes the depth (i.e. along the Z direction) of the laser focal spot location in the eye. Thus, the scan line rotator 4 modifies the lateral orientation of the scan line 12 while the moveable XY scanning stage 7 and the fast-Z scan device 8 move the center of the scan line in X, Y and Z directions. Because the scanning speed of the resonant scanner is typically much faster than the speed of the XY scanning stage and the fast-Z scan device, the scan line 12 may be referred to as a fast scan line, and the movement of the fast scan line in X, Y and Z directions may be referred to as a slow sweep.

The XY scanning stage 7 may be a motorized stage with two motors that drive its movements in the X and Y directions. Preferably, the XY scanning stage is a recoilless stage configured to reduce or eliminate mechanical vibration. The fast-Z scan device 8 may include a voice coil actuator that drives a lens in the Z direction. Movements of the lens lead to a focus depth change. The fast-Z scan frequency may be between 50 Hz and 15,000 Hz.

The patient interface device 9 couples the patient's eye to the ophthalmic surgical laser system 1. The patient interface 9 may include a visualization beam splitter to reflect the light from the eye along an optical path 11 toward a video microscope or ocular microscope 14, to allow the eye to be imaged by an image detector of the microscope. The visualization beam splitter, optical path 11 and microscope 14 are optional.

The auto-Z module 10 may include either a confocal detector or a non-confocal detector, and may be used to measure depth of target surfaces as described in more detail in the above-mentioned U.S. Pat. Appl. Pub. No. 2020/0064622.

The controller 13, which may be implemented by a processor executing suitable machine-readable program code and data stored in a non-volatile memory, is operably coupled to the various components of the system 1 including the laser 2, the fast-Z scan device 8, the resonant scanner 3, the scan line rotator 4, the XY scanning stage 7, the detector 14, and the communication module 15. The controller 13 is configured to direct these components of the system to output the focal spot of the pulsed laser beam in a desired pattern in the eye so as to modify the eye. The communication module 15 provides information to the operator of the laser system 1 at the system and/or remotely via wired or wireless data connection, and may include displays, user input devices such as keyboard, mouse, joystick, etc. The ophthalmic surgical laser system may additionally include an OCT (optical coherence tomography) device (not shown in FIG. 10A) which may be used to measure structures of the target (e.g. eye tissues).

FIG. 10B shows an ophthalmic surgical laser system 20 suitable for making an incision in a target material such as a cornea of an eye. The system 20 includes, but is not limited to, a laser source (not shown) that generates an input pulsed laser beam 21, a fast-Z scan device 22, a resonant scanner 23 for producing a scan line 12B of the pulsed laser beam 21, a scan line rotator 24 for rotating the lateral orientation of the scan line 12B, a beam expander 25, an objective with an adjustable focusing mechanism (slow-Z scanner) 26, a XY scanning stage 27 for deflecting or directing the pulsed laser beam 21 on or within the target, a patient interface 28 that may optionally include a beam splitter, a controller 13B, an optional image detector 29 disposed on an optical path 29A defined by the beam splitter of the patient interface, and a communication module 15B. The slow-Z scanner 26 may be used to set the laser focal spot at a desired focal depth which may set the Z-baseline of the scan pattern.

One difference between the system of FIG. 10B and that of FIG. 10A is that the XY scanning stage 7 in FIG. 10A carries both the objective 6 and other components including the fast-Z scan device 8, resonant scanner 3, scan line rotator 4, and beam expander 5, while the XY scanning stage 27 in FIG. 10B carries the objective 26 but not the other components mentioned above. Note that the in the system of FIG. 10A, the objective 6 may also be equipped with a slow-Z scanner (also represented by reference symbol 6).

Further details of ophthalmic surgical laser systems having the configurations shown in FIGS. 10A and 10B are described in commonly owned U.S. patent application Ser. No. 14/970,898, filed Dec. 16, 2015, entitled "Compact Ultra-Short Pulsed Laser Eye Surgery Workstation," and Ser. No. 14/865,396, filed Sep. 25, 2015, entitled "Systems and Methods for Lenticular Laser Incision," which are incorporated herein by reference in their entireties.

In the above ophthalmic laser systems, the beam scanning can be realized with a "fast-scan-slow-sweep" scanning scheme, also referred herein as a fast-scan line scheme. In one example, the system uses an 8 kHz (e.g. between 7 kHz and 9 kHz) resonant scanner to produce a fast scan line of about 1 mm (e.g., between 0.9 mm and 1.1 mm) and a scan speed of about 25 m/sec, and X, Y, and Z scan mechanisms with the scan speed (sweep speed) smaller than about 0.1 m/sec. The fast scan line may be perpendicular to the optical beam propagation direction, i.e., it is always parallel to the XY plane. The trajectory of the slow sweep can be any three dimensional curve drawn by the X, Y, and Z scanning devices (e.g., XY-scanner and fast-Z scanner). An advantage of the "fast-scan-slow-sweep" scanning scheme is that it only uses small field optics (e.g., a field diameter of 1.5 mm) which can achieve high focus quality at relatively low cost. The large surgical field (e.g., a field diameter of 10 mm or greater) is achieved with the XY-scanner, which may be unlimited.

As described earlier, the flap procedures in various embodiments of the present invention utilize the fast-scan-slow-sweep scanning scheme to form various cuts of the flap. The controller of the laser system controls the various components of the system to form the above-described cuts.

It will be apparent to those skilled in the art that various modification and variations can be made in the corneal flap procedure and related apparatus of the present invention without departing from the spirit or scope of the invention. Thus, it is intended that the present invention cover modifications and variations that come within the scope of the appended claims and their equivalents.

What is claimed is:

1. A method implemented in an ophthalmic surgical laser system for incising a cornea of a patient's eye to form a corneal flap, the patient's eye being coupled to a patient interface device of the ophthalmic surgical laser system, the method comprising:

controlling a laser delivery system of the ophthalmic surgical laser system to deliver a pulsed laser beam to the cornea;

controlling the laser delivery system to scan the pulsed laser beam to form a bed of the flap in the cornea at a predefined bed depth; and controlling the laser delivery system to scan the pulsed laser beam to form a side cut, wherein the side cut extends in lateral directions along a periphery of the bed except for a hinge portion, and extends in a depth direction from the bed depth to an anterior corneal surface, wherein the side cut defines a lower portion and an upper portion separated by an uncut bubble barrier layer, wherein the bubble barrier layer is located within an epithelium of the cornea, and wherein the upper portion of the side cut intersects the anterior corneal surface.

2. The method of claim 1, wherein the bubble barrier layer has a thickness of between 5 and 20 microns.

3. The method of claim 1, wherein the bubble barrier layer is located at a uniform distance from the anterior corneal surface.

4. The method of claim 1, wherein the bubble barrier layer is located at variable distances from the anterior corneal surface.

5. The method of claim 4, wherein the bubble barrier layer form a wave pattern extending in and angular direction of the flap.

6. The method of claim 1, wherein the step of controlling the laser delivery system to scan the pulsed laser beam to form the bed includes forming a ring cut that defines a periphery of the bed, and forming a bed cut in a central portion of the bed surrounded by the ring cut, wherein the side cut is formed before the bed cut.

7. The method of claim 1, wherein the step of controlling the laser delivery system to scan the pulsed laser beam to form the bed includes forming a ring cut that defines a periphery of the bed, and forming a bed cut in a central portion of the bed surrounded by the ring cut, wherein the side cut is formed after the bed cut.

8. The method of claim 1, wherein the step of controlling the laser delivery system to scan the pulsed laser beam to form the side cut includes scanning the laser beam in the depth direction along the side cut and blanking the laser beam in predefined depth ranges when scanning the laser beam in the depth direction.

9. The method of claim 1, further comprising controlling a high frequency scanner of the ophthalmic surgical laser system to scan the pulsed laser beam back and forth to form a laser scan line in the cornea;

wherein the side cut is formed by placing the laser scan line tangent to a circumference of the side cut, moving the laser scan line in a depth direction, simultaneously moving the laser scan line around the circumference, simultaneously rotating the scan line to keep it tangent to the circumference, and blanking the laser beam in predefined depth ranges when moving the laser beam in the depth direction.

10. An ophthalmic surgical laser system comprising:
a laser source configured to generate a laser beam;
a laser delivery system configured to deliver the laser beam to a cornea of a patient's eye; and
a controller configured to control the laser source and the laser delivery system to perform a method for incising a cornea of a patient's eye to form a corneal flap, the patient's eye being coupled to a patient interface device of the ophthalmic surgical laser system, the method comprising:

controlling the laser delivery system to deliver a pulsed laser beam to the cornea;

controlling the laser delivery system to scan the pulsed laser beam to form a bed of the flap in the cornea at a predefined bed depth; and controlling the laser delivery system to scan the pulsed laser beam to form a side cut, wherein the side cut extends in lateral directions along a periphery of the bed except for a hinge portion, and extends in a depth direction from the bed depth to an anterior corneal surface, wherein the side cut defines a lower portion and an upper portion separated by an uncut bubble barrier layer, wherein the bubble barrier layer is located within an epithelium of the cornea, and wherein the upper portion of the side cut intersects the anterior corneal surface.

11. The ophthalmic surgical laser system of claim 10, wherein the bubble barrier layer has a thickness of between 5 and 20 microns.

12. The ophthalmic surgical laser system of claim 10, wherein the bubble barrier layer is located at a uniform distance from the anterior corneal surface.

13. The ophthalmic surgical laser system of claim 10, wherein the bubble barrier layer is located at variable distances from the anterior corneal surface.

14. The ophthalmic surgical laser system of claim 13, wherein the bubble barrier layer form a wave pattern extending in and angular direction of the flap.

15. The ophthalmic surgical laser system of claim 10, wherein the step of controlling the laser delivery system to scan the pulsed laser beam to form the bed includes forming a ring cut that defines a periphery of the bed, and forming a bed cut in a central portion of the bed surrounded by the ring cut, wherein the side cut is formed before the bed cut.

16. The ophthalmic surgical laser system of claim 10, wherein the step of controlling the laser delivery system to scan the pulsed laser beam to form the bed includes forming a ring cut that defines a periphery of the bed, and forming a bed cut in a central portion of the bed surrounded by the ring cut, wherein the side cut is formed after the bed cut.

17. The ophthalmic surgical laser system of claim 10, wherein the step of controlling the laser delivery system to scan the pulsed laser beam to form the side cut includes scanning the laser beam in the depth direction along the side cut and blanking the laser beam in predefined depth ranges when scanning the laser beam in the depth direction.

18. The ophthalmic surgical laser system of claim 10, wherein the method further comprises controlling a high frequency scanner of the ophthalmic surgical laser system to scan the pulsed laser beam back and forth to form a laser scan line in the cornea;

wherein the side cut is formed by placing the laser scan line tangent to a circumference of the side cut, moving the laser scan line in a depth direction, simultaneously moving the laser scan line around the circumference, simultaneously rotating the scan line to keep it tangent to the circumference, and blanking the laser beam in predefined depth ranges when moving the laser beam in the depth direction.

\* \* \* \* \*